United States Patent [19]

Guerra

[11] 4,186,752
[45] Feb. 5, 1980

[54] DEVICE FOR TAKING BLOOD AND FOR INJECTING MEDICATION

[76] Inventor: Luis A. Guerra, 715 Park Ave., New York, N.Y. 10013

[21] Appl. No.: 938,155

[22] Filed: Aug. 30, 1978

[51] Int. Cl.² .............................................. A61B 5/14
[52] U.S. Cl. ...................................... 128/766; 128/221; 128/274; 251/149.5
[58] Field of Search ............ 128/766, 763, 765, 218 N, 128/218 NV, 218 D, 221, 274, 276; 251/149.5, 149.2

[56] References Cited

U.S. PATENT DOCUMENTS

| | | | |
|---|---|---|---|
| 3,143,109 | 8/1964 | Gewertz | 128/276 X |
| 3,181,529 | 5/1965 | Wilburn | 128/DIG. 5 |
| 3,191,905 | 6/1965 | Brown | 251/149.5 |
| 3,230,964 | 1/1966 | Debrotnic et al. | 251/149.5 |
| 3,416,567 | 12/1968 | VonDardel et al. | 128/274 X |
| 3,460,529 | 8/1969 | Leucci | 128/2 F |
| 3,513,829 | 5/1970 | Deuschle et al. | 128/276 X |
| 3,585,996 | 6/1971 | Reynolds et al. | 128/221 X |
| 3,753,432 | 8/1973 | Guerra | 128/DIG. 5 |
| 3,906,930 | 9/1975 | Guerra | 128/2 F |
| 3,996,923 | 12/1976 | Guerra | 128/2 F |

FOREIGN PATENT DOCUMENTS

| | | | |
|---|---|---|---|
| 532192 | 8/1931 | Fed. Rep. of Germany | 128/DIG. 5 |
| 1054174 | 10/1953 | France | 128/221 |
| 743839 | 1/1956 | United Kingdom | 128/218 D |

*Primary Examiner*—Kyle L. Howell
*Attorney, Agent, or Firm*—Blum, Kaplan, Friedman, Silberman & Beran

[57] ABSTRACT

An improved blood-taking device of the type wherein a hypodermic needle is inserted into a blood vessel and one or more evacuated containers in succession are connected to the needle for collecting blood samples comprises a support portion which supports the needle and a container portion including a projecting tube, the tip of which can be joined to the support portion in a combined axial and rotational movement. The container portion includes a valve which can be opened in a continuation of the rotational movement used for joining the tube to the support portion. The structure of the components is such that the valve in the container portion is opened only after the container is joined to the support portion through the tube. Similarly, when the operation of taking blood is complete the tube and container portion are separated from the support portion by a rotation in the opposite direction, the structure of the device being such that the valve is closed before the tube is separated from the support portion.

9 Claims, 4 Drawing Figures

U.S. Patent  Feb. 5, 1980  4,186,752
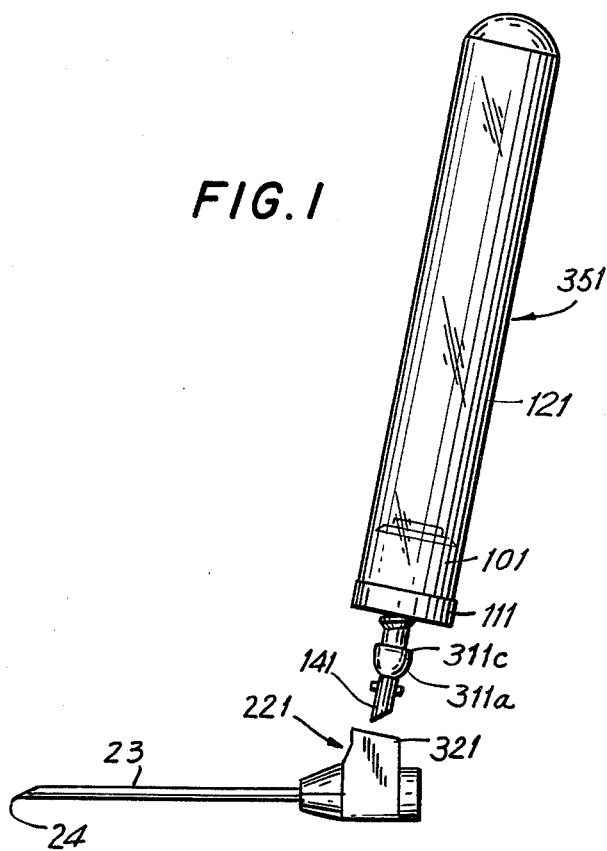
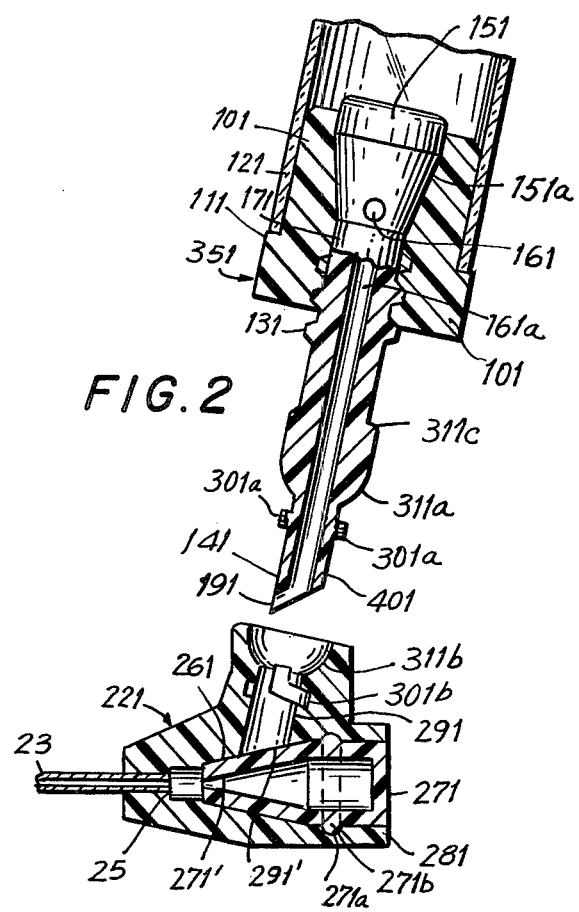
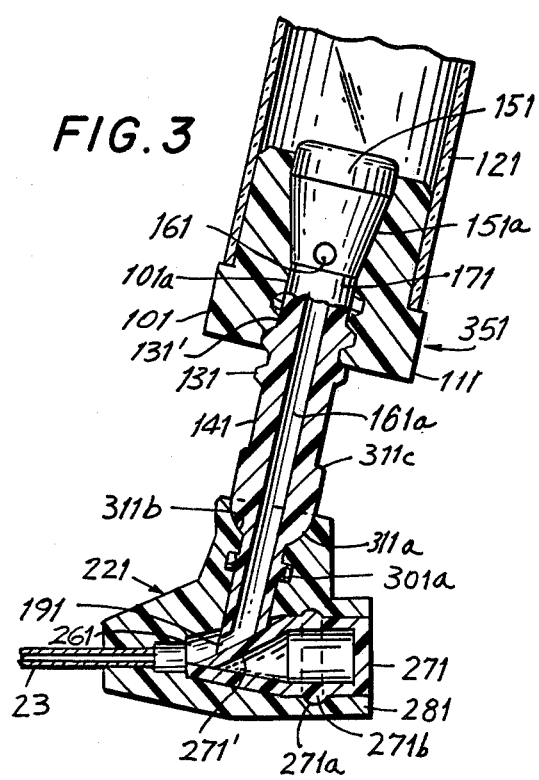
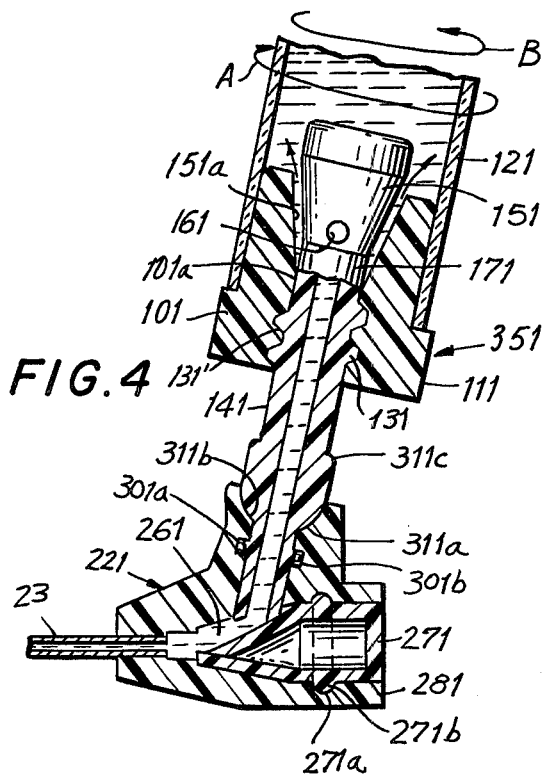

DEVICE FOR TAKING BLOOD AND FOR INJECTING MEDICATION

CROSS REFERENCE TO RELATED APPLICATIONS

The present application is related to Ser. No. 344,387, filed Mar. 23, 1973, now U.S. Pat. No. 3,906,930 and to Ser. No. 598,902, filed July 24, 1975, now U.S. Pat. No. 3,996,923.

BACKGROUND OF THE INVENTION

In the aforenoted patents, it was explained that the conventional double-pointed cannula as used with conventional evacuated containers gave rise to problems of possible contamination, piercing of the fingers of the operators, clotting of the inner tip during the interchange of containers and extravasation of blood from an adjacent vein and hematoma if the outer tip of the double-ended cannula lodges within tissues rather than a vein.

In the earlier embodiments of the device to be described herein, these difficulties were avoided through a construction in which the cannula-containing portion of the device and the container each included a valve. In particular, the container portion included a valve which could be opened gradually, presenting the advantage that should the flow of blood not start almost immediately after cracking the valve, the valve could be shut. This feature provided the advantage of indicating that the needle had not been placed correctly into a vein, thereby alerting the operator to the need for removing the needle and re-inserting same.

Although the earlier embodiments of the present invention successfully overcame the aforenoted disadvantages, it was found that the device was somewhat complex both as to structure and as to method of use, making the device relatively expensive and requiring training of the operator. Accordingly, it became evident that it would be desirable to simplify the construction of the device from the standpoint of operation as well as from the standpoint of cost.

SUMMARY OF THE INVENTION

A blood-taking device is made in two joinable portions, the first portion including a cannula and a support section, and a second portion including an evacuated container closed by a stopper through which passes an axially and rotatably movable tube. The first and second portions, to be referred to hereinafter as the support and container portions respectively, can be firmly joined together to establish a continuous passage for the flow of blood through the cannula, the support section and the tube into the container. The support section has a first valve therein which is ordinarily closed so that when the tube and container portion are not connected to the support portion, blood in the support section is closed off from contact with the air and possible contamination is avoided. The container portion has a second valve therein which makes it possible to control the difference of pressure applied at the distal tip of the cannula and to cut off the application of vacuum in the event that the cannula is not properly placed in a blood vessel from which blood is to be drawn, thereby avoiding the danger of hematoma. The second valve is operated by rotation of the container around the tube. The distal end of the tube can be seated in the proximal end of the support section to make a continuous passage, the distal end of the tube opening the first valve when the container portion and the support portion are connected.

The tube and the container are coaxial and the structures of the join between the tube and the support portion and of the second valve are such that rotation in a single direction while inserting the distal end of the tube into the proximal end of the support section effects both the join and the opening of the second valve. However, the resistance to effecting the join provided by the join structure is substantially less than the resistance provided by the valve structure to opening same. Accordingly, the combination of the two structures provides that the join must be effected before the second valve is opened. Similarly, the join can be broken and the second valve can be closed by a single rotation in the reverse direction used for making the join and opening the second valve. However, the structures are such that the resistance of the valve to closing same is substantially less than the resistance of the join structure to separating the components. Accordingly, the device insures that, at the termination of taking a blood sample, the container will be closed before the container portion is separated from the support portion.

Accordingly, an object of the present invention is to provide an improved blood-taking device having valve means for quickly cutting off the vacuum applied to the tip of a cannula in the event that the cannula is not properly situated in a blood vessel.

Another object of the present invention is to provide an improved blood-taking device with which a plurality of blood specimens can be drawn with a single insertion of a cannula into a blood vessel without incurring the danger of blood clotting in the hiatus between the taking of successive specimens.

An important object of the present invention is to provide an improved blood-taking device in which a blood sample is protected from contamination.

Yet another object of the invention is to provide a hypodermic applicator that allows either to inject soluble drugs into a blood vessel or to draw out blood without spilling due to flush-back.

A significant object of the present invention is to provide an improved blood-taking device in which the operation of said device is free from the danger of causing hematoma.

A most important object of the present invention is an improved blood-taking device in which the joining of the cannula-containing portion to the container portion and opening the valve in the container portion can be effected by rotation of the container portion in a single direction, the structure of the device insuring that the container portion is joined to the support portion prior to opening the valve in the container portion.

Yet a further object of the present invention is an improved blood-taking device in which a cannula-containing portion and a container portion are joined at a breakable seal, and in which a valve in the container portion is closed and the seal is broken by rotation of the container portion in a single direction, the structure of the device being such that closing of the container prior to separating the container portion from the support portion is insured.

Still other objects and advantages of the invention will in part be obvious and will in part be apparent from the specification.

The invention accordingly comprises an article of manufacture possessing the features, properties, and the relation of elements which will be exemplified in the article hereinafter described and the scope of the invention will be indicated in the claims.

BRIEF DESCRIPTION OF THE DRAWING

For a fuller understanding of the invention, reference is had to the followng description taken in connection with the accompanying drawing, in which:

FIG. 1 is a side view of a device in accordance with the present invention with the cannula-containing portion and the container portion separated;

FIG. 2 is a side view in section of the device in accordance with the present invention with the two portions thereof in position for joining;

FIG. 3 is a side view in section showing the two portions of the device connected together, and with the valve in the container portion closed; and FIG. 4 is a side view similar to that of FIG. 3 but with the valve in the container portion open.

DESCRIPTION OF THE PREFERRED EMBODIMENT

The improved blood-taking device of the present invention consists of two joinable portions, a support portion 221 and a container portion 351 shown separated from each other in FIG. 1. Cannula 23 has a sharp tip 24 for insertion into a blood vessel through the skin of a subject. Proximal end 25 (FIG. 2) of cannula 23 is tightly held in support portion 221 having a passage 261 therethrough. Plug 271 having flexible walls is seated in passage end 281. The flexible wall of plug 271 lies across opening 291' of aperture, i.e., socket 291, so that plug 271 seals opening 291' and passage end 281 simultaneously.

Aperture 291 is fitted with grooves 301b for forming a bayonet join together with lugs 201a on the surface of tube 141. As is evident, the bayonet may be the inverse of that shown in the Figures, thus, the groove 301b may be formed on tube 141 and the lugs 301a be disposed within aperture 291 of support portion 221 (not shown). Aperture 291 terminates in a hemispherical socket 311b at the proximal end thereof. Passage 261 preferably has a groove 271a for receiving a corresponding ridge on the surface of plug 271 which may be either hollow or solid the ridge and groove serving to hold said plug in place.

Container 121 is closed by stopper 101 having a flange 111 which seats on the open end of container 121. Stopper 101 has an axial passage therethrough traversed by tube 141 which fits within stopper 101 sufficiently tightly to prevent the entry of air between tube 141 and the axial passage in stopper 101, but not so tightly as to prevent axial or rotational movement of tube 141 in stopper 101. The interface between stopper 101 and tube 141 may be lubricated with an inert silicone grease.

Tube 141 is closed at its proximal end 151 which is frustoconical in shape. Frustoconical section 151 performs the double function of sealing the proximal end of tube 141 and simultaneously limiting the axial excursion of container 121 in the proximal direction by seating in a mating socket 151a in stopper 101.

Tube 141 has a lateral opening 161 therein located a short distance away from the sealed end of tube 141, preferably on the lateral portion of frustoconical section 151. As shown in FIG. 2, opening 161 lies within the passage through stopper 101, thus effectively sealing container 121 against the entry of air when container 121 is evacuated. In a preferred form the axial passage through stopper 101 is threaded from the exterior portion thereof inwardly to a distance short of that at which opening 161 will be positioned when section 151 is seated in the mating portion 151a of stopper 101. As is obvious, tube 141 must be correspondingly threaded.

FIG. 2 shows the container portion of the device about to be joined to the support portion. The join is effected by inserting the distal tip 191 of tube 141 in aperture or passage 291. Tip portion 401 of tube 141 and aperture 291 are preferably shaped so that they mate closely preventing leakage of air therebetween. As tip 191 is inserted into aperture 291, upper portion 271' of plug 271 is displaced downwardly, thereby establishing a continuous passage through opening 291 from the tip of cannula 23 to the interior of tube 141. This is shown in FIG. 3 in which the upper wall 271' of flexible plug 271 is depressed by tip 191. The appearance of the support portion of the device after insertion of tip 191 into aperture 291 is shown in section in FIGS. 3 and 4.

When it is desired to take a blood sample, container portion 351 must first be joined with support portion 221. Accordingly, tip 191 of tube 141 is inserted into socket 291 in support portion 221. Lugs 301a enter grooves 301b in support portion 221 and a twist of the container portion 351 in the direction indicated by the arrow A in FIG. 4 effects a bayonet lock between lugs 310a and grooves 301b. Also, socket 291 has a spherical portion 311b which mates with a corresponding spherical portion 311a on tube 141, effecting a tight seal between the support and container portions. Preferably, tip portion 401 also fits tightly within passage 291 to effect a seal also.

As would be expected, the engagement of tip 401 with socket 291, of lugs 311a with grooves 301b and of hemispherical portions 311a and 301b with each other requires the overcoming of some slight frictional resistance. These resistances are sensed by the operator as a weak resistance to rotation of the container portion 351 in the direction indicated by the arrow A. The significance of this weak resistance will become apparent in connection with the method by which valve 171 in container portion 351 is opened for the flow of blood thereinto.

Valve 171, in the preferred construction shown in FIGS. 2, 3 and 4, comprises a frustoconical section 151 at the proximal end of tube 141, the actual end of tube 141 being closed. A lateral opening 161 on the side wall of tube 141 connects with passage 161a through tube 141. In preparation for use, frustocone 151a is firmly seated in stopper 101 which, preferably, is of an elastic rubber. In this condition, lateral opening 161 may be sealed by contact with stopper 101. In addition, frustoconical surface 151a is firmly engaged by stopper 101 so that neither air nor blood can pass between passage 161a and the interior of container 121. Also, the exterior wall 141a of tube 141 engages the interior of stopper 101 firmly enough so that air cannot pass between the exterior of the tube and the interior of stopper 101, thereby insuring that the container will remain sealed at all times, so far as access by air is concerned.

FIG. 2 shows the two parts of the device ready to be joined and FIG. 3 shows the device when tube 141 has been inserted into passage 291 and container portion 351 has been rotated far enough to join the two portions sealingly. As will be noted, frustocone 151 is still seated firmly in stopper 101.

To open valve 171, rotation of container 121 in the direction of the arrow A is continued. Tube 141 and stopper 101 have corresponding threads 131 and 131' in an orientation such that rotation of container 121 in the direction of arrow A moves the container axially toward the support portion 221, thus moving frustocone 151 gradually out of engagement with stopper 101. However, the nature of the rubber is such that considerable resistance is encountered in disengaging frustocone 151 from stopper 101 when said frustocone is fully seated. Since the resistance to disengaging frustocone 151 from stopper 101 is considerably greater than that encountered in joining the container portion to the support portion of the device, it is thereby insured that inserting tip 401 into passage 291 and rotating the container will first effect a tight join between the container and support portions as the bayonet lock is effected and only then when at the end of the bayonet lock will valve 171 be opened to the extent desired. A further point to be noted is that as the container 121 is rotated to take the frustocone out of the fully seated condition, the valve 171 passes through a state in which the resistance to rotation is substantially decreased but in which the valve is as yet tightly closed. This state may be termed the partly-seated condition. That such a state is possible follows from the fact that the stopper 101 is of an elastic material so that it releases its grip gradually upon the frustocone. The sequence of resistances to turning of the container 121 relative to support portion 221 insures that as container portion 351 and support portion 221 are united and the container is rotated, there will first be effected a tightly-sealed connection between the support portion and the tube 141, after which frustocone 151 will be freed from the tight grip of the interior surface of stopper 101. Finally, an annular channel will be gradually opened between frustocone 151 and stopper 101 so that blood can be drawn by the vacuum within container 121 through cannula 23, passage 261, passage 161a and into container 121.

As described in my patents, U.S. Pat. No. 3,906,930 and U.S. Pat. No. 3,996,923, both of which are incorporated herein by reference and which are to be regarded as fully presented herein, it is important that it be possible to provide for opening valve 171 gradually, and the present embodiment of my invention provides for this possibility.

When a desired quantity of blood has been drawn, container portion 351 is separated from support portion 221 so that said container portion may be delivered to a laboratory for analysis of the contents of tube 121. In the process of separation of said portions, it is essential that valve 171 be closed prior to separation of the portions in order that the contents of the container may remain uncontaminated. This sequence of events is achieved by providing that the resistance of valve 171 to closure by rotating container 121 in the direction of arrow B shall be less than the resistance afforded by tube 141 and support portion 221 in separating same. It should be noted that closure of the valve 171 takes place when frustocone 151 is brought to the aforenoted partly-seated condition, so that it is unnecessary to bring said frustocone to the fully-seated position to effect closure of valve 171 and sealing of the contents of container 121. As to separation of tube 141 from passage 291 in support portion 221, this step involves, for instance, rotation of the spherical surface 311a against hemispherical socket 311b which entails considerable friction. In addition, there is the friction involved in the separation of lugs 301a from grooves 301b. The total resistance to rotation of tube 141 within support portion 221 in the disengagement process is therefore substantially greater than the resistance encountered in bringing frustocone 151 to the partly-seated position. Accordingly, a single rotation by the operator of container 121 in the direction of the arrow B first seals container 121 by closing valve 171 and only then disengages the container portion from the support portion of the device. Disengagement is facilitated by the biasing force of wall 271' of stopper 271 as it attempts to return to its original shape as shown in FIG. 2. The container, with the valve in partly-seated state, is then ready for shipment. If desired, the operator can rotate the container relative to tube 141 to bring the frustocone 151 to the fully-seated position, but this is unnecessary. As will be seen from the foregoing, the structure of the two portions of my blood-taking device makes it possible to join said two portions and open a container portion by rotating the container in a single direction and to insure that the two portions will be joined before the container is opened. Similarly, the structure makes it possible to seal the container and to separate the container from the support portion by a single rotation in a single direction while insuring that the container is sealed before the container portion is separated from the support portion. The operation of the device is sufficiently simple so that it required only a minimum of instructions and guarantees that the various steps involved in putting the device into operation and separating the container for shipment to a laboratory will be taken in the correct order. Also, excessive rotation of the container in the direction of the arrow A is prevented by the presence of surface 311c. As the container is rotated it moves in the distal direction until stopper 101 makes contact with surface 311c, thus stopping the rotation of the container.

It will thus be seen that the objects set forth above, among those made apparent from the preceding description, are efficiently attained and, since certain changes may be made in the above article without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A device for taking blood from a blood vessel, comprising a support portion having a passage therethrough, a cannula at the distal end of said support portion, an evacuable container portion, elastic stopper means in the distal end of said evacuable container portion and disposed for rotation therewith, tube means passing through said stopper means, said support portion having a socket at the proximal end of said passage, the distal end of said tube means hereinafter termed "tip", being shaped to join with said socket for forming a continuous passage through said tube means and said support portion, said stopper means and the proximal end of said tube means forming a first valve means for gradually connecting the passage in said tube means with the interior of said container portion by rotation of said container portion in a first direction relative to said tube means, said tip being shaped to join with said socket by rotation in said first direction and to present a first resistance in joining said tip with said socket, said proximal end of said tube means being shaped for passing from a fully seated position to a partly seated position and thence gradually to a position in which said valve means is fully open when said container portion is rotated in said first direction, said valve means being fully closed when said tube means is in the fully and partly seated positions, said tube means presenting a second resistance, greater than said first resistance, when moving said tube means from said fully-seated to said partly-seated position by rotation of said container portion, said tube means and said evacuable container portion being essentially coaxial, whereby inserting said tip in said socket when said tube means is fully seated, and continuously rotating said container in said first direction first joins said tip to said socket, and only then moves said tube means from fully-seated to partially seated position, whence the valve means can be opened to any selected extent by further rotation in said first direction, thereby insuring that said container portion is joined to said support before said first valve means is opened.

2. The device as defined in claim 1, wherein said tip and socket are shaped for disengaging same when said tube means is rotated in the direction opposite to said first direction and hereinafter termed "second" direction, said tip and socket presenting a third resistance to said rotation of said tip in said second direction, said valve means being shaped for passing from open position to said partly seated position by rotation of said container portion in said second direction and for presenting a fourth resistance which is substantially smaller than said third resistance, thereby providing that continued rotation of said container portion in said second direction will first close said valve means and isolated blood in said container portion before separating said container portion from said portion.

3. The device as defined in claim 1, wherein said tip and socket are shaped to form a bayonet connection.

4. The device as defined in claim 1, wherein the exterior of said tube means and the interior of said stopper means are threaded for mutual engagement, the proximal end of said tube means being frustoconical in shape with the larger base of said frustocone at the proximal end of said tube means, said tube means being free of an opening on the proximal end thereof and having an opening on the side-wall thereof connecting with the passage of said tube means, said fully-seated position being that in which a major portion of said frustocone is within said elastic stopper means and said side-wall opening is well-removed from the proximal end of said stopper means, said partly seated position being that in which said opening is far enough within said stopper means so that fluid is prevented from traversing said opening.

5. The device as defined in claim 1, wherein said support section has therein second valve means proximate said socket, said second valve means being constructed for opening by insertion of said tip in said socket.

6. The device as defined in claim 5, wherein said second valve means includes a flexible plug, said second valve being operable by deflection of a wall of said plug by said tip.

7. The device as defined in claim 1, wherein said socket and tip are shaped for forming a liquid-tight seal against traversal of said seal by liquid between the interior and the exterior of said device.

8. The device as defined in claim 4, wherein the diameter of said larger base of said frustocone is large enough to serve as a stop against continued rotation of said container portion in said second direction.

9. The device as defined in claim 1, wherein said tube means has a region of expanded diameter positioned for providing a stop against excessive rotation of said container portion in said first direction, by engaging the distal end of said stopper means.

* * * * *